US008652085B2

(12) United States Patent
Gelvin et al.

(10) Patent No.: US 8,652,085 B2
(45) Date of Patent: Feb. 18, 2014

(54) REDUCTION OF GAS ESCAPE IN MEMBRANE ACTUATORS

(75) Inventors: Michael L. Gelvin, Alta Loma, CA (US); Cesario P. Dos Santos, Aliso Viejo, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 93 days.

(21) Appl. No.: 13/539,567

(22) Filed: Jul. 2, 2012

(65) Prior Publication Data

US 2014/0005587 A1    Jan. 2, 2014

(51) Int. Cl.
*A61M 5/00* (2006.01)
(52) U.S. Cl.
USPC .................................................. 604/9; 604/8
(58) Field of Classification Search
USPC ..................... 604/8, 9; 607/88, 92, 94; 600/9
See application file for complete search history.

(56) References Cited

U.S. PATENT DOCUMENTS

| | | | |
|---|---|---|---|
| 4,089,329 A | 5/1978 | Couvillon et al. | |
| 4,206,762 A | 6/1980 | Cosman | |
| 4,457,757 A | 7/1984 | Molteno | |
| 4,656,827 A | 4/1987 | Puillet | |
| 4,750,901 A | 6/1988 | Molteno | |
| 4,922,913 A | 5/1990 | Waters et al. | |
| 5,005,577 A | 4/1991 | Frenkel | |
| 5,178,604 A | 1/1993 | Baerveldt | |
| 5,179,953 A | 1/1993 | Kursar | |
| 5,397,300 A | 3/1995 | Baerveldt | |
| 5,476,445 A | 12/1995 | Baerveldt | |
| 5,558,629 A | 9/1996 | Baerveldt | |
| 5,910,110 A | 6/1999 | Bastable | |
| 6,007,511 A | 12/1999 | Prywes | |
| 6,048,328 A * | 4/2000 | Haller et al. | 604/288.03 |
| 6,447,449 B1 | 9/2002 | Fleischman et al. | |
| 6,468,283 B1 | 10/2002 | Richter et al. | |
| 6,579,235 B1 | 6/2003 | Abita et al. | |
| 6,589,198 B1 | 7/2003 | Soltanpour et al. | |

(Continued)

FOREIGN PATENT DOCUMENTS

| | | |
|---|---|---|
| DE | 4438201 | 5/1996 |
| EP | 2427097 | 3/2012 |

(Continued)

OTHER PUBLICATIONS

Byunghoon Bae, Hongseok Kee, Seonho Kim, Yeon Lee, Taeseok Sim, Yongkweon Him and Kyihwan Park; "In Vitro Experiment of the Pressure Regulating Valve for a Glaucoma Impact"; Journal of Micromechanics and Microengineering, 13 (2003); pp. 613-619.

(Continued)

*Primary Examiner* — Leslie Deak
(74) *Attorney, Agent, or Firm* — Kenneth D. Bassinger

(57) ABSTRACT

A membrane actuator device includes a housing with an entrance port and an exit port connected by a fluid flow passageway. A gas generation chamber is disposed within the housing, the gas generation chamber comprising a first opening and a gas generating element. A membrane actuation chamber has a second opening and may be defined at least in part by a flexible membrane configured to deflect and affect fluid flow through the fluid flow passageway. A barrier spans the width of the first opening of the gas generation chamber and is disposed in a manner that reduces the likelihood that gas molecules will pass from the gas generation chamber to the membrane actuation chamber.

22 Claims, 5 Drawing Sheets

(56) References Cited

U.S. PATENT DOCUMENTS

| | | |
|---|---|---|
| 6,682,500 B2 | 1/2004 | Soltanpour et al. |
| 6,712,764 B2 | 3/2004 | Jeffries et al. |
| 6,749,568 B2 | 6/2004 | Fleischman et al. |
| 6,939,299 B1 | 9/2005 | Petersen et al. |
| 7,137,952 B2 | 11/2006 | Leonardi et al. |
| 7,169,106 B2 | 1/2007 | Fleischman et al. |
| 7,252,006 B2 | 8/2007 | Tai et al. |
| 7,354,416 B2 | 4/2008 | Quiroz-Mercado et al. |
| 7,409,863 B2 | 8/2008 | Bateman et al. |
| 7,612,328 B2 | 11/2009 | Kaiser |
| 8,182,435 B2 | 5/2012 | Dacquay et al. |
| 8,257,295 B2 | 9/2012 | Rickard et al. |
| 2001/0000527 A1 | 4/2001 | Yaron et al. |
| 2002/0019607 A1 | 2/2002 | Bui |
| 2002/0049374 A1 | 4/2002 | Abrea |
| 2002/0099359 A1 | 7/2002 | Santini, Jr. et al. |
| 2002/0143284 A1 | 10/2002 | Tu et al. |
| 2002/0193674 A1 | 12/2002 | Fleischman et al. |
| 2003/0078487 A1 | 4/2003 | Jeffries et al. |
| 2003/0225318 A1 | 12/2003 | Montegrande et al. |
| 2004/0059248 A1 | 3/2004 | Messner et al. |
| 2004/0073137 A1 | 4/2004 | Lloyd et al. |
| 2004/0111050 A1 | 6/2004 | Smedley et al. |
| 2004/0116794 A1 | 6/2004 | Wolfgang et al. |
| 2004/0186367 A1 | 9/2004 | Fresco |
| 2004/0254438 A1 | 12/2004 | Chuck et al. |
| 2004/0254517 A1 | 12/2004 | Quiroz-Mercado et al. |
| 2005/0049578 A1 | 3/2005 | Tu et al. |
| 2005/0159660 A1 | 7/2005 | Montegrande et al. |
| 2005/0271704 A1 | 12/2005 | Tu et al. |
| 2005/0273033 A1 | 12/2005 | Grahn et al. |
| 2006/0131350 A1 | 6/2006 | Schechter et al. |
| 2007/0019156 A1 | 1/2007 | Fink |
| 2007/0032757 A1 | 2/2007 | Medow et al. |
| 2007/0106199 A1 | 5/2007 | Krivoy et al. |
| 2007/0109117 A1 | 5/2007 | Heitzmann et al. |
| 2007/0123767 A1 | 5/2007 | Montegrande et al. |
| 2007/0129623 A1 | 6/2007 | Fleischmann et al. |
| 2007/0212397 A1 | 9/2007 | Roth |
| 2008/0015421 A1 | 1/2008 | Penner |
| 2008/0077127 A1 | 3/2008 | Gao et al. |
| 2008/0125691 A1 | 5/2008 | Yaron et al. |
| 2008/0129486 A1 | 6/2008 | Jeckelmann et al. |
| 2008/0228127 A1 | 9/2008 | Burns et al. |
| 2009/0069648 A1 | 3/2009 | Irazqui et al. |
| 2009/0076367 A1 | 3/2009 | Sit et al. |
| 2009/0143713 A1 | 6/2009 | Van Dam et al. |
| 2009/0227933 A1 | 9/2009 | Karageozian |
| 2009/0275924 A1 | 11/2009 | Lattanzio et al. |
| 2009/0312742 A1 | 12/2009 | Pang et al. |
| 2010/0010416 A1 | 1/2010 | Juan, Jr. et al. |
| 2010/0042209 A1 | 2/2010 | Guarnieri |
| 2010/0121248 A1 | 5/2010 | Van Der Burg et al. |
| 2010/0234717 A1 | 9/2010 | Wismer |
| 2010/0253167 A1 | 10/2010 | Clifford et al. |
| 2011/0046536 A1 | 2/2011 | Stegmann et al. |
| 2011/0071454 A1 | 3/2011 | Santos et al. |
| 2011/0071456 A1 | 3/2011 | Rickard |
| 2011/0248671 A1 | 10/2011 | Santos et al. |

FOREIGN PATENT DOCUMENTS

| | | |
|---|---|---|
| WO | WO 93/03665 | 3/1993 |
| WO | WO 98/03665 | 1/1998 |
| WO | WO 99/38470 A2 | 8/1999 |
| WO | WO 99/38470 A3 | 10/1999 |
| WO | WO 01/94784 | 12/2001 |
| WO | WO 03/001991 | 1/2003 |
| WO | WO 03/102632 | 12/2003 |
| WO | WO 2007/127305 A2 | 11/2007 |
| WO | WO 2007/136993 A1 | 11/2007 |
| WO | WO 2008/061043 A2 | 5/2008 |
| WO | WO 2008/061043 A3 | 9/2008 |
| WO | WO 2009/026499 | 2/2009 |
| WO | WO 2009/049686 | 4/2009 |
| WO | WO 2009/081031 A2 | 7/2009 |
| WO | WO 2009/081031 A3 | 9/2009 |
| WO | WO 2010/129446 A1 | 11/2010 |
| WO | WO 2011/034727 A1 | 3/2011 |
| WO | WO 2011/034738 A1 | 3/2011 |
| WO | WO 2011/034740 A1 | 3/2011 |
| WO | WO 2011/034742 A2 | 3/2011 |
| WO | WO 2011/035218 A1 | 3/2011 |
| WO | WO 2011/034742 A3 | 5/2011 |

OTHER PUBLICATIONS

Eggers, T., et al, "Wireless Intra-Ocular Pressure Monitoring System Integrated Into an Artificial Lens," 1st Annual Int'l IEEE-EMBS Special Topic Conference on Microtechnologies in Medicine & Biology, Oct. 12-14, 2000, pp. 466-469, Lyon, France.

Greene, M.E. and Gilman, B.G., "Intraocular Pressure Measurement With Instrumented Contact Lenses," Investigative Ophthalmology & Visual Science (IVOS), Apr. 1974, pp. 299-302, vol. 13, No. 4, IVOS.

Hjortdal, Jesper and Jensen, Peter, "In Vitro Measurement of Corneal Strain, Thickness, and Curvature Using Digital Image Processing," Acta Ophthalmologica Scandinavica, 1995, pp. 5-11, vol. 73, Denmark.

International Searching Authority, Search Report and Written Opinion of the International Searching Authority, PCT/US2010/033329, Jul. 13, 2010, 14 pages.

International Searching Authority, Search Report and Written Opinion of the International Searching Authority, PCT/US2010/047429, Nov. 1, 2010, 15 pages.

International Searching Authority, Search Report and Written Opinion of the International Searching Authority, PCT/US2010/047600, Dec. 14, 2010, 13 pages.

International Searching Authority, Search Report and Written Opinion of the International Searching Authority, PCT/US2010/049424, Nov. 26, 2010, 15 pages.

International Searching Authority, Search Report of the International Searching Authority, PCT/US2011/036742, Aug. 17, 2011, 2 pages.

Lam, Andrew K.C. and Douthwaite, William A., "The Effect of an Artificially Intraocular Pressure on the Central Corneal Curvature," Ophthalmic and Physiological Optics, 1997, pp. 18-24, vol. 17, No. 1, Elsevier Science, Ltd., Great Britain.

Leonardi, Matteo, et al., "A Soft Contact Lens With a Mems Strain Gage Embedded for Intraocular Pressure Monitoring," In Proc. 12th Int'l Conference on Solid State Sensors, Actuators and Microsystems, Jun. 8-12, 2003, pp. 1043-1046, vol. 2, Boston, MA.

Leonardi, Matteo, et al., "First Steps Toward Noninvasive Intraocular Pressure Monitoring with a Sensing Contact Lens," Investigative Ophthalmology & Visual Science (IVOS), 2004, pp. 3113-3117, vol. 45, No. 9, IVOS.

McLaren, Jay W., et al, "Continuous Measurement of Intraocular Pressure in Rabbits by Telemetry," Investigative Ophthalmology & Visual Science (IVOS), May 1996, pp. 966-975, vol. 37, No. 6, IVOS.

Mokwa, Wilfried, et al, "Micro-Transponder Systems for Medical Applications," IEEE Transactions on Instrumentation and Measurement, Dec. 2001, pp. 1551-1555, vol. 50, No. 6, IEEE, Germany.

Puers, Robert, "Linking Sensors with Telemetry: Impact on the System Design," In Proc. 8th Int'l Conference of Solid State Sensors, Actuators, Eurosens, Jun. 25-29, 1995, pp. 169-174, Stockholm, Sweden.

Schnakenberg, U., et al, "Initial Investigations on Systems for Measuring Intraocular Pressure," Sensors and Actuators, 2000, p. 287-291, vol. 85, Elsevier Science B.V., Germany.

Stangel, Karsten, et al, "A Programmable Intraocular CMOS Pressure Sensor System Implant," IEEE Journal of Solid-State Circuits, Jul. 2001, pp. 1094-1100, vol. 36, No. 7, IEEE, Germany.

Ullerich, Stella, et al, "Micro Coils for an Advanced System for Measuring Intraocular Pressure," 1st Annual Int'l IEEE-EMBS Special Topic Conference on Microtechnologies in Medicine & Biology, Oct. 12-14, 2000, pp. 470-474, Lyon, France.

Van Schuylenbergh, K., et al, "An Implantable Telemetric Tonometer for Direct Intraocular Pressure Measurements," 1st European Conference on Biomedical Engineering, Feb. 1991, pp. 194-195, vol. 17, No. 20, Nice, France.

(56) References Cited

OTHER PUBLICATIONS

Walter, Peter; Intraocular Pressure Sensor: Where Are We—Where Will We Go? Journal Graefe's Archive For Clinical and Experimental Ophthalmology; Publisher Springer Berline/Heidelberg; ISSN 0721-832X (Print) 1435-702X (Online); Issue vol. 240, No. 5/May 2002 DOI 10.1007/s00417-002-0474-y; pp. 335-336; Subject Collection Medicine.

International Searching Authority, Written Opinion of the International Searching Authority, PCT/US2010/047605, Dec. 16, 2010, 9 pages.

International Searching Authority, International Search Report of the International Searching Authority, PCT/US2010/047612, Dec. 21, 2010, 7 pages.

International Searching Authority, Written Opinion of the International Searching Authority, PCT/US2010/047612, Dec. 21, 2010, 10 pages.

Nisar A., Afzulpurkar Nitin, Mahaisavariya Banchong, and Tuantranont Adisorn; "MEMS-Based Micropumps in Drug Delivery and Biomedical Applications"; ScienceDirect; Sensors and Actuators B 130 (2008) pp. 917-942.

Neagu Cristina R.; "A Medical Microactuator Based on an Electrochemical Principle"; Thesis at the Twente University,the Netherlands, Enschede; Aug. 28, 1998; pp. 1-162.

Saloomeh Saati MD., Ronalee Lo PhD, Po-Ping Li PhD, Ellis Meng PhD, Rohit Varma MD MPH, and Mark S. Humayun MD PhD; "Mini Drug Pump for Ophthalmic Use"; TRANS Am Ophthalmol Soc 2009; 107; pp. 60-71.

Erik Stemme and Goran Stemme; "A Valveless Diffuser/Nozzle-Based Fluid Pump"; ScienceDirect; Sensors and Actuators A, 39 (1993); pp. 159-167.

\* cited by examiner

REDUCTION OF GAS ESCAPE IN MEMBRANE ACTUATORS

BACKGROUND

The present disclosure relates generally to membrane actuator devices and associated systems and methods for use in ophthalmic treatments.

Glaucoma, a group of eye diseases affecting the retina and optic nerve, is one of the leading causes of blindness worldwide. Most forms of glaucoma result when the intraocular pressure (IOP) increases to pressures above normal for prolonged periods of time. IOP can increase due to high resistance to the drainage of the aqueous humor relative to its production. Left untreated, an elevated IOP causes irreversible damage to the optic nerve and retinal fibers resulting in a progressive, permanent loss of vision.

The eye's ciliary body continuously produces aqueous humor, the clear fluid that fills the anterior segment of the eye (the space between the cornea and lens). The aqueous humor flows out of the anterior chamber (the space between the cornea and iris) through the trabecular meshwork and the uveoscleral pathways, both of which contribute to the aqueous humor drainage system. The delicate balance between the production and drainage of aqueous humor determines the eye's IOP.

FIG. 1 is a diagram of the front portion of an eye that helps to explain the processes of glaucoma. In FIG. 1, representations of the lens 10, cornea 20, iris 30, ciliary body 40, trabecular meshwork 50, Schlemm's canal 60, and anterior chamber 70 are pictured. Anatomically, the anterior segment of the eye includes the structures that cause elevated IOP which may lead to glaucoma. Aqueous humor fluid is produced by the ciliary body 40 which lies beneath the iris 30 and adjacent to the lens 10 in the anterior segment of the eye. This aqueous humor washes over the lens 10 and iris 30 and flows to the drainage system located in the angle of the anterior chamber 70. The angle of the anterior chamber 70, which extends circumferentially around the eye, contains structures that allow the aqueous humor to drain. The trabecular meshwork 50 is commonly implicated in glaucoma. The trabecular meshwork 50 extends circumferentially around the anterior chamber 70. The trabecular meshwork 50 seems to act as a filter, limiting the outflow of aqueous humor and providing a back pressure that directly relates to IOP. Schlemm's canal 60 is located beyond the trabecular meshwork 50. Schlemm's canal 60 is fluidically coupled to collector channels (not shown) allowing aqueous humor to flow out of the anterior chamber 70. The two arrows in the anterior segment of FIG. 1 show the flow of aqueous humor from the ciliary bodies 40, over the lens 10, over the iris 30, through the trabecular meshwork 50, and into Schlemm's canal 60 and its collector channels.

One method of treating glaucoma includes implanting a drainage device in a patient's eye. The drainage device allows fluid to flow from the interior chamber of the eye to a drainage site, relieving pressure in the eye and thus lowering TOP. In order to provide consistency and accuracy in fluid flow through the drainage device, it may be important to limit changes and degradation that may occur in the drainage device over time.

The system and methods disclosed herein overcome one or more of the deficiencies of the prior art.

SUMMARY

In one exemplary aspect, the present disclosure is directed to a membrane actuator device. The device includes a housing including an entrance port and an exit port connected by a fluid flow passageway. A gas generation chamber is disposed within the housing, the gas generation chamber comprising a first opening and a gas generating element. A membrane actuation chamber has a second opening and may be defined at least in part by a flexible membrane configured to deflect and affect fluid flow through the fluid flow passageway. A barrier spans the width of the first opening of the gas generation chamber and is disposed in a manner that reduces the likelihood that gas molecules will pass from the gas generation chamber to the membrane actuation chamber.

In one aspect, the gas generation chamber comprises a plurality of sidewalls and comprises electrodes disposed along a first sidewall of the plurality of sidewalls, the first opening disposed along a second sidewall of the plurality of sidewalls, the first sidewall being adjacent the second sidewall. In one aspect, the barrier is disposed within the gas generation chamber.

In another aspect, the present disclosure is directed to a membrane actuator device for implantation in an eye of a patient to treat an ocular condition. The device may include a housing including an entrance port and an exit port connected by a fluid flow passageway and a gas generation chamber within the housing. The gas generation chamber may include a first opening and a gas generating element. A membrane actuation chamber may have a second opening and may be defined at least in part by a flexible membrane configured to deflect into and affect fluid flow through the fluid flow passageway. A passageway may extend between and connect the first opening of the gas generation chamber and the second opening of the membrane actuation chamber in a manner that a pressure change in the gas generation chamber results in a corresponding pressure change in the membrane actuation chamber. A barrier may be configured to limit the introduction of gas from the gas generation chamber into the membrane actuation chamber.

In another exemplary aspect, the present disclosure is directed to a method of regulating drainage from an anterior chamber of an eye with a membrane valve. The method may include directing fluid through a fluid flow passageway formed within a housing. The fluid flow passageway may comprise a portion formed of a flexible membrane. The membrane may separate the fluid flow passageway from a membrane actuation chamber. The method may also include modifying pressure in a gas generation chamber connected to the membrane actuation chamber in a manner that a pressure change in the gas generation chamber results in a pressure change in the membrane actuation chamber. The passage of gas may be limited from the gas generation chamber to the membrane actuation chamber with a barrier shaped and configured to at least partially block gas from entering the membrane actuation chamber. In one aspect, limiting the passage of gas comprises at least partially blocking the gas with a barrier spanning the width of an opening to a passageway extending between the gas generation chamber and the membrane actuation chamber.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

Figure 1:
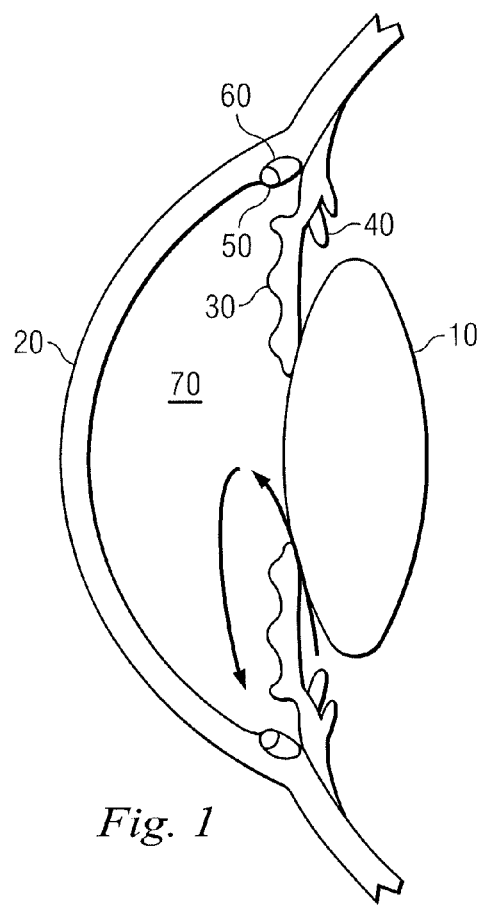
FIG. 1 is a diagram of the front portion of an eye.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure relates generally to electrolysis-based membrane actuator devices for draining fluid from an anterior chamber, and in particular to devices that reduce opportunity for actuating gas to escape the actuator device within electrolysis-based membrane actuator devices. Electrolysis-based membrane actuator devices utilize deflection of the membrane in response to pressure differentials across the membrane to regulate the flow through the device. These pressure differentials may be obtained using phase-change processes that convert liquid to gas. However, gas molecules in membrane valves may diffuse through the membrane. As gas is lost through the membrane, a gas imbalance arises due to the unequal diffusion rates of various gases (e.g., hydrogen and oxygen, which have vastly different diffusion rates due to their molecular size difference). In addition, such devices may require a continuous supply of energy to generate sufficient gas through electrolysis to overcome both the loss of gas through the membrane and the gas recombination in order to maintain desired membrane deflection behavior.

Such electrolysis-based membrane actuator devices include, by way of non-limiting example, valves and pumps. In some instances, embodiments of the present disclosure are configured to be part of an IOP control system. Those of skill in the art will realize that the flow control chambers disclosed herein may be utilized in similar applications requiring minimal or selective gas diffusion through a membrane.

The electrolysis-based membrane actuator devices disclosed herein are configured to reduce the diffusion rate of gas through the membrane and provide for a controlled increase in the rate of gaseous recombination within the flow control chamber, thereby increasing the longevity, reliability, and speed of valve actuation. In particular, each of the electrolysis-based membrane actuator devices of the present disclosure include a fluid-filled gas generation chamber and a separate membrane actuation chamber. These are connected by a passage-way and barrier features that restrict passage of gas from the gas generation chamber to the membrane actuation chamber. In addition, since the chambers isolate the gas from the membrane, they reduce the inadvertent escape of gas through the membrane that may arise in IOP control systems utilizing electrolysis-based devices with single-compartment flow control chambers. The reduction in the escape of gas through the membrane provides an increase in the longevity and the reliability of device actuation by maintaining balance of the gas molecular ratio within the flow control chamber. Thus, the flow control chambers disclosed herein may optimize the performance of electrolysis-based devices utilizing membrane actuators within an IOP control system.

Figure 2:
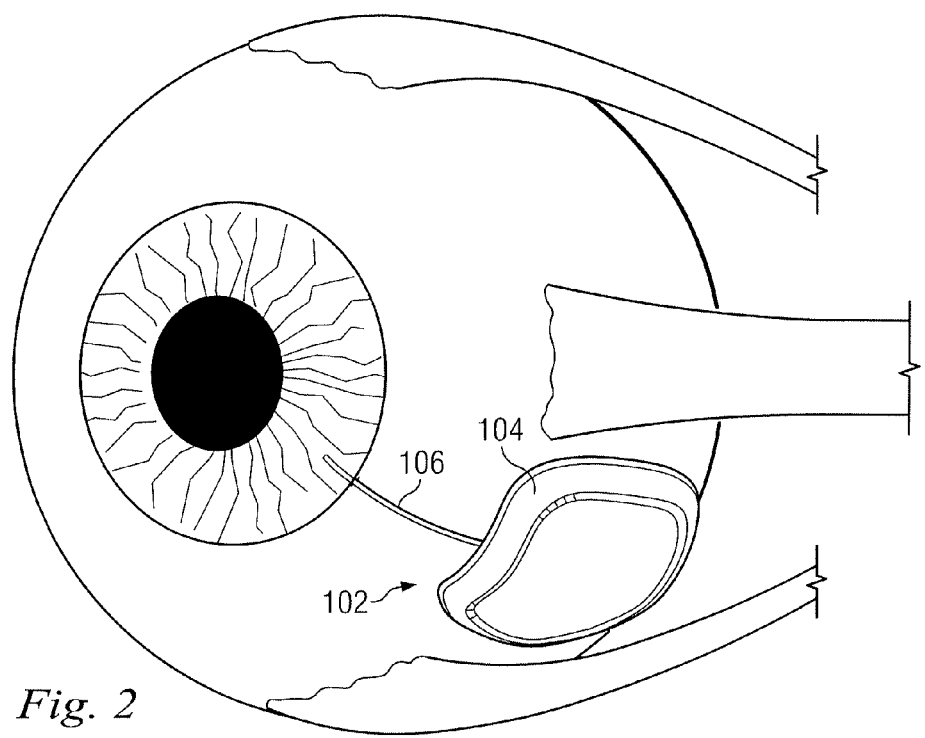
FIG. 2 is an illustration of an exemplary membrane actuator disposed in the eye in accordance with one embodiment of the present disclosure.

FIG. 2 shows an exemplary ocular implantable membrane actuator 102 disposed on an eye according to one exemplary aspect of the present disclosure. The membrane actuator 102 includes a body referred to herein as a plate 104 and a drainage tube 106 that extends from the plate 104. The plate 104 is arranged to carry various components of an IOP control system, and may include a valve, pump, transducers or sensors, a processing system and memory, drug delivery components, a power source or other components that may be used to either control the membrane actuator 102 or otherwise treat ocular conditions.

The plate 104 is configured to fit at least partially within the subconjunctival space and is sized for example within a range between about 15 mm×12 mm to about 30 mm×15 mm and has a thickness less than about 2 mm thick and preferably less than about 1 mm thick. The plate 104 may be formed to the radius of the eye globe (about 0.5 inches). It may be rigid and preformed with a curvature suitable to substantially conform to the globe or it may be flexible to conform to the globe. Some embodiments are small enough that conforming to the globe provides little benefit in comfort or implantation technique. The above dimensions are exemplary only, and other sizes and arrangements are contemplated. When implanted, the plate 104 may be located in the subconjunctival pocket between the conjunctiva and sclera. It may be generally located on an ocular quadrant commonly used for conventional glaucoma drainage devices with plates; that is, it may be centered such that it is equidistant from the neighboring ocular muscles that define the ocular quadrant chosen for implantation.

The drainage tube 106 is sized to bridge the anterior chamber and the plate 104 in the subconjunctival pocket to provide an auxiliary flow path for aqueous humor, bypassing the flow-resistive conventional pathway through the trabecular meshwork and shunting aqueous humor directly to a drainage site. In the example shown, the drainage tube 106 is a single tube having a single lumen. Other embodiments include a plurality of drainage tubes or a plurality of lumens cooperating together to permit fluid to flow through the membrane actuator 102. The drainage tube 106 is sized to extend from the plate 104 to the anterior chamber of the eye, as shown in FIG. 2. Aqueous humor may drain through the drainage tube from the anterior chamber to and out of the plate 104 to alleviate elevated intraocular pressure conditions.

Figure 3:
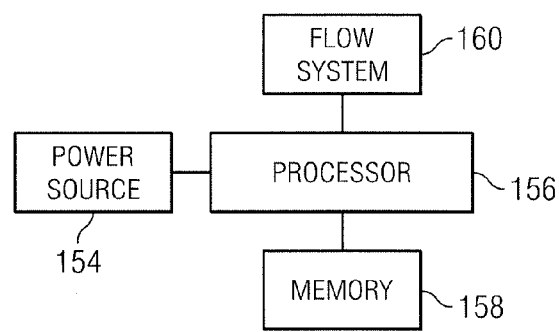
FIG. 3 is a block diagram of an exemplary IOP control system according to the principles of the present disclosure.

FIG. 3 is a block diagram of an exemplary IOP control system 150 forming a part of the membrane actuator 102. The IOP control system 150 is configured in a manner that provides IOP pressure control, reducing complications arising from surgical implant glaucoma treatments. In FIG. 3, the IOP control system 150 includes a power source 154, a processor 156, a memory 158, and a flow system 160.

The power source 154, which provides power to the system 150, is typically a rechargeable battery, such as a lithium ion or lithium polymer battery, although other types of batteries may be employed. The power source can be recharged via inductive coupling such as an RFID link or other type of magnetic coupling.

The processor 156 is typically an integrated circuit with power, input, and output pins capable of performing logic functions. In various embodiments, the processor 156 may be a targeted device controller or a microprocessor configured to control more than one component of the device.

The memory 158, which is typically a semiconductor memory such as RAM, FRAM, or flash memory, interfaces with the processor 156. As such, the processor 156 can write to and read from the memory 158, and perform other common functions associated with managing semiconductor memory. In this manner, a series of IOP readings can be stored in the memory 158.

The flow system 160 controls the amount of drainage flow through the membrane actuator 102. In one embodiment, it is responsive to signals from the processor 156 to increase flow, decrease flow, or maintain flow.

The flow system 160 may be controlled by the processor 156 based on input data received from, by way of non-limiting example, sensors or data or a programmed treatment plan. A desired pressure differential (that corresponds to a flow rate) can be maintained by controlling the operation of the flow system 160. Likewise, various intraocular pressure parameters, such as, by way of non-limiting example, the desired IOP, the IOP change rate, and/or the bleb pressure may be controlled by controlling the operation of flow system 160.

Figure 4:
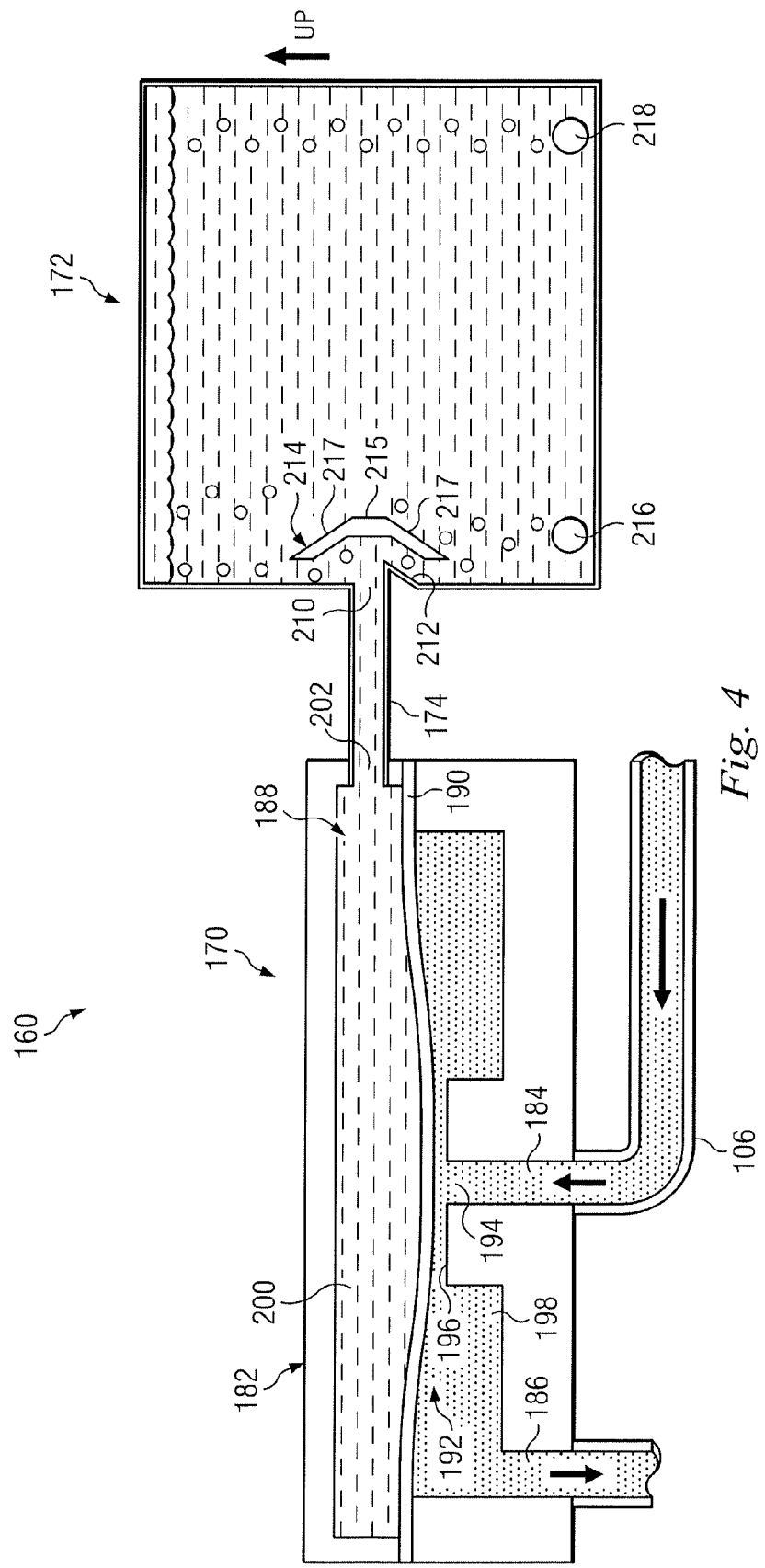
FIG. 4 is a schematic illustration of an exemplary flow system of the IOP control system including an exemplary membrane valve in accordance with one embodiment of the present disclosure.

FIG. 4 shows a stylized cross-sectional view of an exemplary flow system 160 carried by or forming a part of the plate 104. The flow system 160 includes a membrane system 170 and a gas generation chamber 172 connected to the membrane system 170 by a passageway 174. The membrane system 170 is formed of a housing 182 with an entrance port 184 and an exit port 186, a flow control system 188 with a flexible membrane 190 in the housing 182, and a fluid flow passageway 192 extending between the entrance port 184 and the exit port 186. The entrance port 184 connects to the drainage tube 106 (FIG. 2) and is configured to receive aqueous flowing from the drainage tube 106. The exit port 186 permits fluid to exit the housing 182 for release at a drainage site or for further regulation.

In the example shown, the passageway 192 includes a first portion 194 extending adjacent a boss 196 that is arranged to cooperate with the flow control system 188 to control drainage fluid flow, and a second, larger portion 198 configured in the embodiment shown as a chamber adjacent the boss 196, that less actively impacts the flow through the plate 106. In accordance with this, the first portion 194 of the fluid flow passageway 192 is formed to be substantially perpendicular to the general plane of the flexible membrane 190, and the upper surface of the boss 196 is arranged to be substantially parallel to the general plane of the flexible membrane 190. As such, flow through the first portion 194 is directed in the direction of and directly at the flexible membrane 190. Because of this, the drainage fluid is forced to redirect at an angle of about 90 degrees, although other angles are contemplated. Because of this arrangement, the flexible membrane 190 in this exemplary embodiment can more easily displace only slightly, but still provide a significant modification in the drainage flow. This occurs because the flexible membrane 190 may act in some respects as a cap on the first portion 194 of the fluid flow passageway. In some aspects, the flexible membrane 190 is arranged to cover the entire upper surface of the boss 196, and may even stretch to extend at least partially along the sides of the boss 196 adjacent the edge between the top of the boss 196 and the sides. Accordingly, in such embodiments, the flexible membrane 190 may largely limit or entirely cut off flow through the membrane actuator 102.

Some alternative examples of the fluid flow passageway 192 include flexible membrane material that may displace to affect fluid flow through the passageway from more than one direction. In some examples, the flexible membrane 190 acts as a toroid or sphincter, with the passageway extending through the hollow center or orifice. In other examples the flexible membrane 190 is disposed on two sides of the passageway 192. In some of these examples, the sides are on opposing sides of the passageway 192. Some of these embodiments may have two or more separate flexible membranes that cooperate to limit the cross-sectional area of the fluid flow passageway 192.

The flexible membrane 190 may be formed of an elastically deformable elastomeric including without limitation, materials such as a silicone, silicon nitride, silicone elastomeric, polyimide, parylene and others. In the example shown, the flexible membrane is secured to the housing 182 at its edges. In one embodiment, the flexible membrane 190 is a circular material secured at its periphery to the housing 182. In other embodiments, the housing 182 and flexible membrane 190 are formed so that the membrane has a non-circular shape, including oval, substantially rectangular, or square, for example. Other shapes are also contemplated.

The flow system 188 includes a membrane actuation chamber 200. The flexible membrane 190 forms the membrane actuation chamber 200 that connects via an opening 202 to the passage 174. Pressure fluctuations cause fluid to travel through the passage 174 and result in membrane deflection, increasing and decreasing the size of the amount of the passageway 192, and likewise, permitting and restricting the amount of fluid that can flow through the passageway 192. This is discussed further below.

The gas generation chamber 172 is in fluid communication with the membrane actuation chamber 200 of the membrane system 170. The gas generation chamber 172 includes an opening 210 connecting to the passageway 174 and physical barrier 212, 214 disposed adjacent the opening 210. The gas generation chamber 172 is fluid filled with an actuator liquid and includes electrodes 216, 218 disposed within the actuator liquid in a manner permitting at least a portion of the ions and electrolytes in the actuator liquid to phase change from liquid to gas, forming gas-filled bubbles within the gas generation chamber 172 through electrolysis. As the gas bubbles form, the pressure in the gas generation chamber 172 increases, thereby causing displacement of fluid through the opening 210, increasing the pressure in the membrane actuation chamber 200 and displacing the membrane 190. This increased pressure in the actuation chamber 200 acts on the membrane 190 to cause its displacement into the fluid flow passageway 192. The electrodes 216, 218 are in electrical communication with the power source 154, which is controlled by the processor 156. Through the electrolysis, water in the actuator liquid may result in hydrogen and oxygen molecules. In some embodiments, the electrodes 216, 218 may be interdigitated for efficient and effective electrolysis.

The opening 210 and the physical barriers 212, 214 in the gas generation chamber 172 are arranged to limit the likelihood of generated gas escaping into the passageway 174. In FIG. 4, the barrier 212 is formed in the wall adjacent the opening 210 and protrudes inwardly into the gas generation chamber 172. Accordingly, the mouth of the opening 210 is not necessarily flush with the wall of the gas generation chamber 172, but is offset inwardly from the wall. In FIG. 4, gas bubbles generated by the electrodes rise past the opening 210 and the barrier 212. The barrier 212 disrupts the bubble path by forcing the bubbles to deflect around the barrier 212, leading them away from the wall having the opening 210 and causing them to travel in a path less likely to align with the opening 210. A second barrier 214 is disposed in the gas generation chamber 172 in a manner that is spaced from, but covers the opening 210. That is, barrier 214 is disposed at a location normal to the direction of the opening 210, such that the barrier 214 prevents bubbles or fluid from entering the opening directly, but the bubbles must change direction to enter the passageway. As can be seen in FIG. 4, the barrier 214 is spaced from and not in contact with the walls of the gas generation chamber 172. Thus, the barrier 214 forms an island in the gas generating chamber. In the example shown, the barrier 214 includes walls angled or oblique relative to the chamber wall in order to cause bubbles that contact the wall to move in a direction away from the opening 210. Here, the barrier 214 is curved to have a central portion 215 disposed at and covering or spanning the opening 210 and has end portions 217 that extend in the direction of the passage. Accordingly, the barrier 214 results in less opportunity and less chance for the bubbles to enter the passageway 174 or the membrane actuation chamber 200 and reduces the likelihood that gas may diffuse through the membrane 190.

The passageway 174 in FIG. 4 allows free-flow of fluid between the gas generation chamber 172 and the membrane actuation chamber 200. Accordingly, any change in pressure or volume in the gas generation chamber 172 results in a corresponding pressure of volume change in the membrane actuation chamber 200. As such, a volume change that occurs as liquid converts to gas in the gas generation chamber results in fluid displaced toward the membrane actuation chamber 200 causing deflection of the membrane 190. The passage and chamber configurations, along with the barriers 212, 214, limit a chance of contact between the gas and the membrane 190. Therefore, the opportunity for the gas to escape the system by diffusing through the membrane is greatly minimized, thereby maintaining the gas ratio and reducing the inadvertent loss of pressure by diffusion. In the example in FIG. 4, the passageway 174 is shown as a connecting tube connecting two spaced chambers. However, the length of the passageway 174 can be any suitable length, and in some embodiments, the length of the passageway 174 is equal to the thickness of a wall of the gas generation chamber 172, and may be equal to the thickness of a wall separating the gas generation chamber 172 and the membrane actuation chamber 200.

Figure 5:
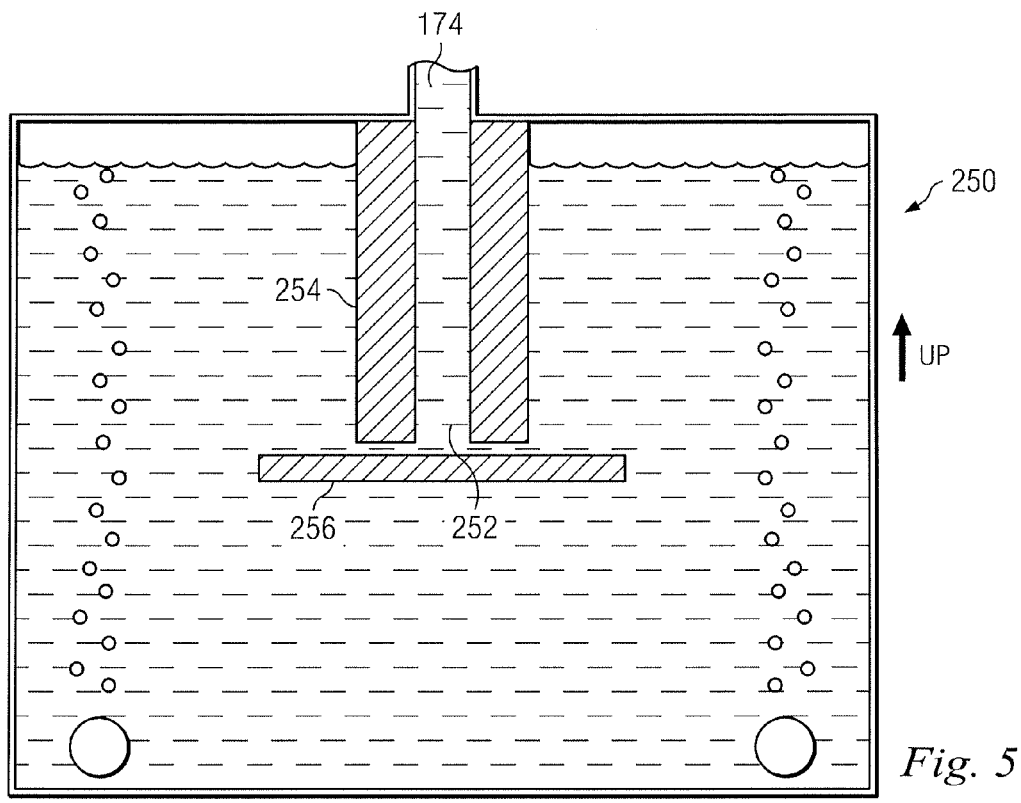
FIG. 5 is an illustration of a gas generation chamber of the flow system in accordance with one embodiment of the present disclosure.

FIG. 5 shows an alternative gas generation chamber, referenced herein by the numeral 250. Similar to the gas generation chamber discussed above, the gas generation chamber 250 includes electrodes that generate bubbles and includes an opening 252 to a passageway to the membrane actuation chamber and barriers 254, 256 that restrict gas from exiting the gas generation chamber 250. In this example the barrier 254 comprises a wall structure extending on both sides of the passage toward a central region of the chamber 250. The opening 252 to the passage is disposed in a central region of one of the sidewalls and the wall structure of the barrier 254 extends on both sides of the opening 252. Accordingly, the opening is disposed substantially centrally in the chamber 250. The barrier 256 is disposed in front of, but spaced apart from the opening 255 so that fluid can flow into the opening as the volume changes within the chamber 255. The barrier 256 in this example extends in a direction normal to the opening and has a length greater than the diameter or width of the opening 252 when viewed in cross-section. In this example, the barrier 256 extends beyond either side of the barrier 254 of the wall structures. Further, the distance between the opening 252 and the barrier 256 is smaller than the width of the opening 252 itself.

Figure 6:
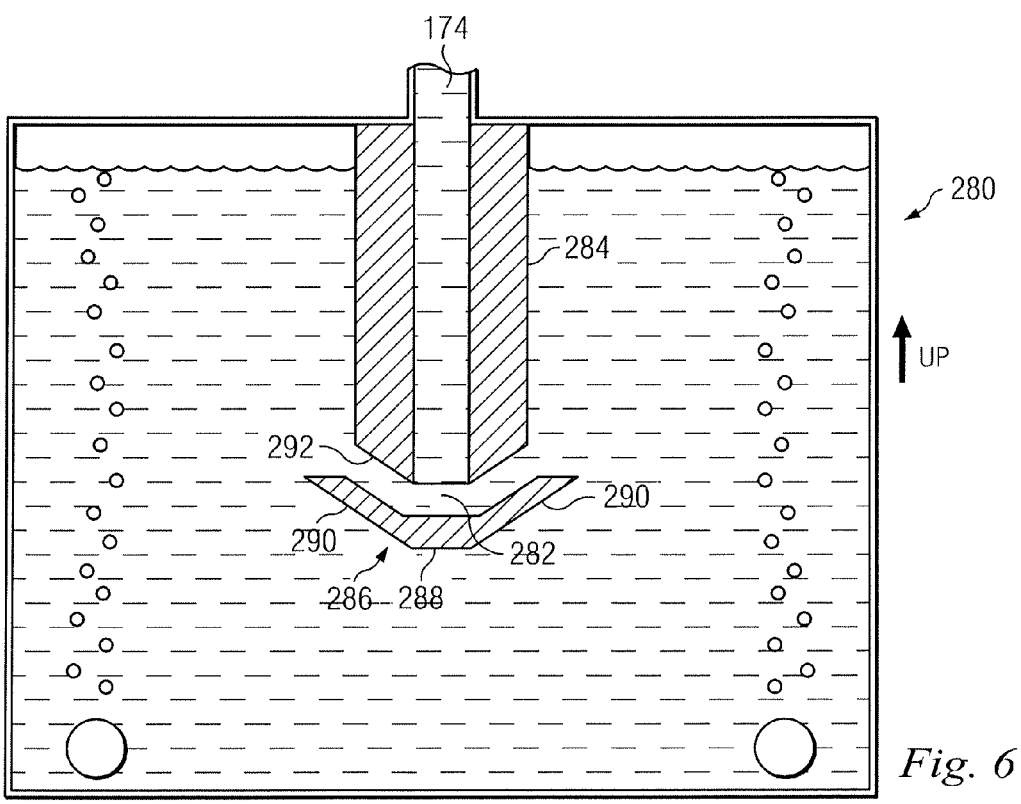
FIG. 6 is an illustration of a gas generation chamber of the flow system in accordance with one embodiment of the present disclosure.

FIG. 6 shows an alternative gas generation chamber, referenced herein by the numeral 280. Similar to the gas generation chamber discussed above, the gas generation chamber 280 includes electrodes that generate bubbles and includes an opening 282 to a passageway to the membrane actuation chamber and barriers 284, 286 that restrict gas from exiting the gas generation chamber 280. In this example the barrier 256 is curved to have a central portion 288 disposed at the opening 282 and has end portions 290 that extend in the direction of the passage. The ends 290 form a hollow central region having a depth sufficient that the opening 282 is disposed in the central region between the ends 290. Accordingly, bubbles that contact the barrier 256 cannot inter the opening without deviating from their course. In this example, the sidewalls of the barrier 284 disposed adjacent the opening include a taper 292 that corresponds to the obliquely extending side portions of the barrier 286.

Figure 7:
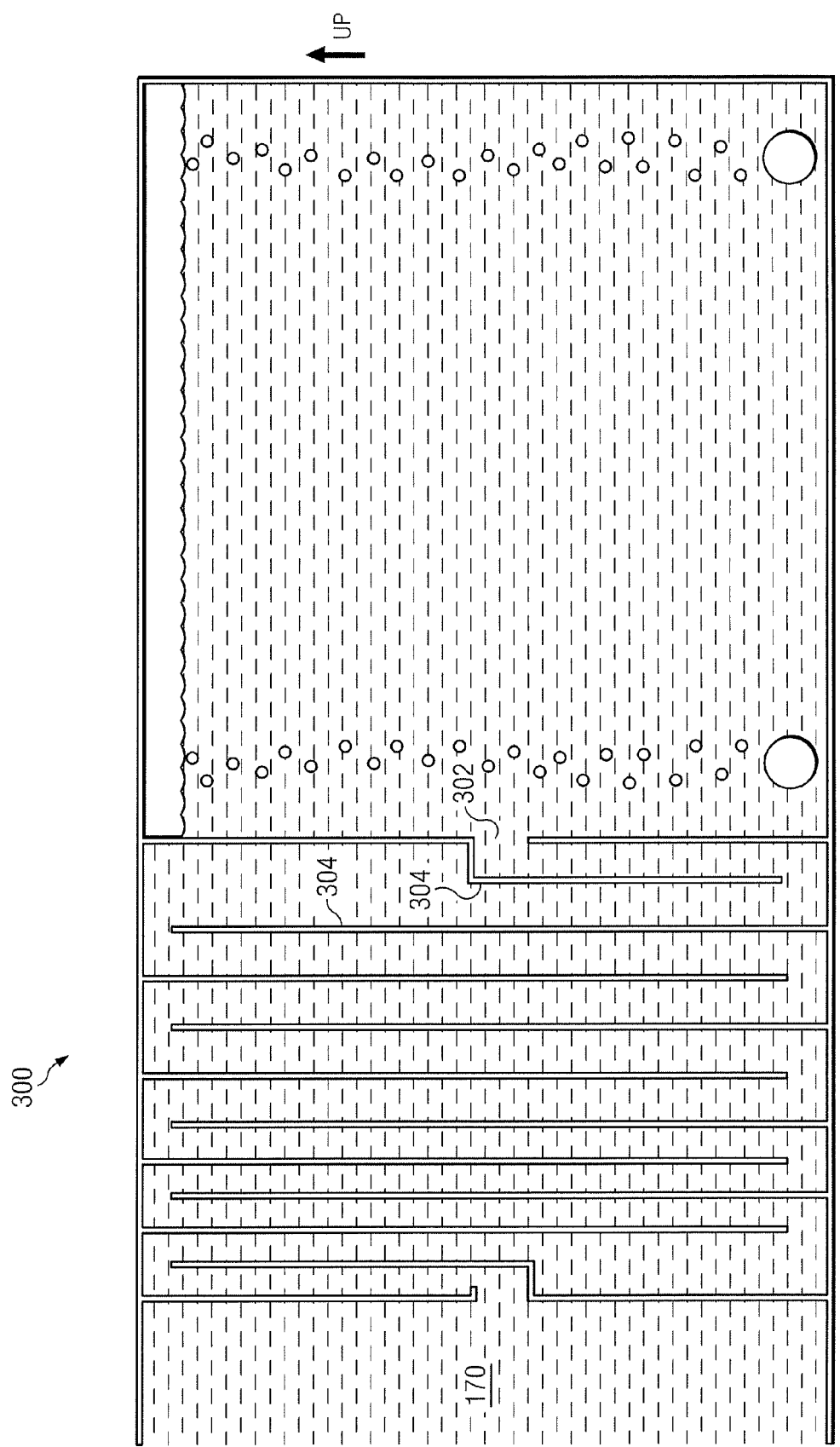
FIG. 7 is an illustration of a gas generation chamber with an elongated passageway of the flow system in accordance with one embodiment of the present disclosure.

FIG. 7 shows an alternative gas generation chamber, referenced herein by the numeral 300. Similar to the gas generation chamber discussed above, the gas generation chamber 300 includes electrodes that generate bubbles and includes an opening 302 to a passageway to the membrane actuation chamber 200. In this example, barriers 304 are formed as a plurality of walls extending in opposite directions in a manner forming a serpentine shape creating a passageway having a length substantially greater than the straight-line distance between the membrane actuation chamber 200 and the gas generation chamber 300. In this example, the passageway has a length extending at least twice the length of the distance between the membrane actuation chamber 200 and the gas generation chamber 300. Depending on the embodiment, the passageway has a length extending at least three times, at least four times, at least five times, the length of the distance between the membrane actuation chamber 200 and the gas generation chamber 300. This may be accomplished by having two barrier walls forming the passageway aligned substantially transverse to a longitudinal axis extending through a central portion of both the membrane actuation chamber 200 and the gas generation chamber 300. Other embodiments have three walls, four walls, five walls, or more walls extending as shown in FIG. 5. FIG. 5 includes at least nine walls. This arrangement of barriers as walls increases the length of the passageway to such a degree that as bubbles may enter the passageway, the time it would take to navigate around the barriers would be greater than the time it would take for the gas molecules to recombine and return to a liquid state. Accordingly, at least most of the molecules in the gaseous state would phase change to the liquid state prior to reaching the membrane actuation chamber and therefore would not diffuse through the membrane.

Figure 8:
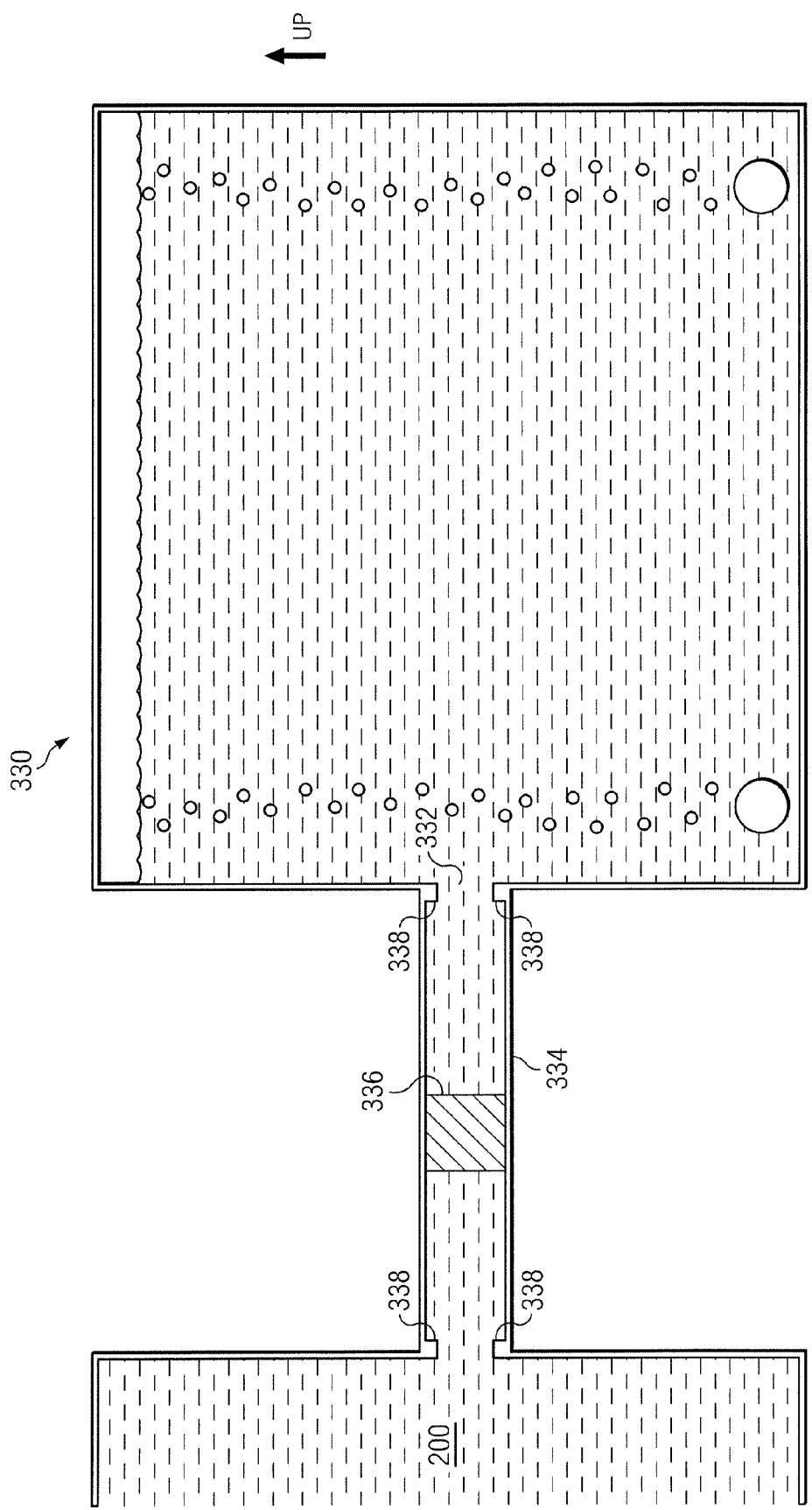
FIG. 8 is an illustration of a gas generation chamber with a piston barrier in the passageway of the flow system in accordance with one embodiment of the present disclosure.

FIG. 8 shows another alternative gas generation chamber, referenced herein by the numeral 330. Similar to the gas generation chamber discussed above, the gas generation chamber 330 includes electrodes that generate bubbles and includes an opening 332 to a passageway 334 to the membrane actuation chamber 200. In this example, a barrier is disclosed as a piston 336 acting within the passageway 334. The piston isolates fluid and gas in the gas generation chamber 330 from fluid in the membrane actuation chamber 200. Accordingly, it is a physical barrier that unlike the membrane, does not permit diffusion of gas therethrough. The piston slides along the passageway according to pressure differentials between the chambers 330, 200. The passage includes physical stops 338 that limit the amount of travel of the piston barrier 336 and prevent the piston from entering the chambers and exiting the passageway.

In use, a surgeon may implant the membrane actuator 102 in a patient's body, such as, in the example, shown, the patient's eye. In one example, the membrane actuator 102 detects pressure at various locations, including for example, at the anterior chamber, such as at a location representative of anterior chamber pressure, and at atmospheric, such as at a location having a pressure that may be correlated to atmospheric. These may be detected with the pressure sensors in communication with the processor 156 of the control system 150. With the pressure known, the control system 150 may be used to adjust the pressure differentials, such as IOP, by controlling the flow system 160. The processor 156 may control the flow system 160 by powering the electrodes in the gas generation chamber to generate bubbles or to not generate bubbles to phase change liquid in the chamber from fluid to gas or to permit the gas molecules to phase change back to liquid at a rate faster than gas is generated. These phase changes increase and decrease the pressure in the gas generation chamber. As the pressure fluctuates, and since the membrane actuation chamber is responsive to the pressure and fluid changes in the gas generation chamber, the pressure in the membrane actuation chamber correspondingly increases or decreases and the membrane 190 is displaced into or out of the fluid flow passageway that allows the passage of fluid from a first region of the body to a second region of the body. The barriers restrict the ability of gas bubbles to pass through the passageway into the membrane actuation chamber. In one embodiment, the liquid includes a catalyst that increases the recombination rate of the gas molecules.

The systems and methods described herein achieve IOP control with very low power and with a very small device. The electrolysis-based devices, systems, and methods disclosed herein accomplish this using electrolysis and a multi-chamber flow system to affect drainage flow. The embodiments of the present disclosure also take into account gas permeability and gas recombination in regulating drainage flow. In particular, these embodiments include a multi-chamber flow system capable of slowing the escape of gas and of being controlled in a way that increases the rate of gaseous recombination in an electrolysis-based membrane actuator device. The multi-chamber flow system allows for the reduction in gas permeability within the system, thereby increasing the longevity and reliability of system actuation by aiding the gas molecular ratio to stay in balance. In addition, an embodiment of the multi-chamber flow system described herein may be controlled to increase the recombination rate of gas molecules within the chamber to facilitate rapid valve actuation. By preventing inadvertent gas imbalance and allowing for rapid valve actuation, the multi-chamber flow system reduces the need for constant energy to power the device. Thus, the devices, systems, and methods disclosed herein may reduce the diffusion rate of gas through the membrane and increase the rate of gaseous recombination within the flow system, thereby increasing the longevity, reliability, and speed of valve actuation.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure

What is claimed is:

1. A membrane actuator device, comprising:
 a housing including an entrance port and an exit port connected by a fluid flow passageway;
 a gas generation chamber within the housing, the gas generation chamber comprising a first opening and a gas generating element;
 a membrane actuation chamber having a second opening and being defined at least in part by a flexible membrane configured to deflect and affect fluid flow through the fluid flow passageway; and
 a barrier spanning the width of the first opening of the gas generation chamber and being disposed in a manner that reduces the likelihood that gas molecules will pass from the gas generation chamber to the membrane actuation chamber.

2. The membrane actuator device of claim 1, wherein the gas generation chamber comprises a plurality of sidewalls and comprises electrodes disposed along a first sidewall of the plurality of sidewalls, the first opening disposed along a second sidewall of the plurality of sidewalls, the first sidewall being adjacent the second sidewall.

3. The membrane actuator device of claim 1, wherein the barrier is disposed within the gas generation chamber.

4. The membrane actuator device of claim 1, wherein the barrier is curved and has a length greater than a width of the first opening, the barrier being disposed to extend in a direction substantially normal to the passageway at the first opening.

5. The membrane actuator device of claim 1, wherein the barrier is a slidable piston separating fluid in the gas generation chamber from fluid in the membrane actuation chamber.

6. The membrane actuator device of claim 1, wherein the barrier comprises a plurality of parallel wall structures.

7. The membrane actuator device of claim 1, wherein the barrier comprises a deviation in a sidewall, the deviation comprising a tapered surface configured to direct rising gas bubbles away from the first opening.

8. The membrane actuator device of claim 1, wherein the length of the passageway is the same thickness as a wall of the generation chamber.

9. The membrane actuator device of claim 1, wherein the flow control chamber includes an actuator liquid and an electrolysis system configured to affect the flow control chamber pressure by converting at least a portion of the actuator liquid to a gas.

10. The membrane actuator device of claim 6, wherein the flow control chamber includes at least one catalyst to increase a recombination rate of the first gas and the second gas.

11. A membrane actuator device for implantation in an eye of a patient to treat an ocular condition, comprising:
- a housing including an entrance port and an exit port connected by a fluid flow passageway;
- a gas generation chamber within the housing, the gas generation chamber comprising a first opening and a gas generating element;
- a membrane actuation chamber having a second opening and being defined at least in part by a flexible membrane configured to deflect into and affect fluid flow through the fluid flow passageway;
- a passageway extending between and connecting the first opening of the gas generation chamber and the second opening of the membrane actuation chamber in a manner that a pressure change in the gas generation chamber results in a corresponding pressure change in the membrane actuation chamber; and
- a barrier configured to limit the introduction of gas from the gas generation chamber into the membrane actuation chamber.

12. The membrane actuator device of claim 11, wherein the gas generation chamber comprises a plurality of sidewalls and comprises electrodes along a first sidewall of the plurality of sidewalls, the first opening being disposed along a second sidewall of the plurality of sidewalls, the first sidewall being adjacent the second sidewall.

13. The membrane actuator device of claim 11, wherein the barrier is disposed within the gas generation chamber.

14. The membrane actuator device of claim 11, wherein the barrier is curved and has a length greater than a width of the first opening, the barrier being disposed to extend in a direction substantially normal to the passageway at the first opening.

15. The membrane actuator device of claim 11, wherein the barrier is a slidable piston separating fluid in the gas generation chamber from fluid in the membrane actuation chamber.

16. The membrane actuator device of claim 11, wherein the barrier comprises a plurality of parallel wall structures.

17. The membrane actuator device of claim 11, wherein the barrier comprises a deviation in a sidewall, the barrier comprising a tapered surface configured to direct rising gas bubbles away from the first opening.

18. A method of regulating drainage from an anterior chamber of an eye with a membrane valve, comprising:
- directing fluid through a fluid flow passageway formed within a housing, the fluid flow passageway comprising a portion formed of a flexible membrane, the membrane separating the fluid flow passageway from a membrane actuation chamber;
- modifying pressure in a gas generation chamber connected to the membrane actuation chamber in a manner that a pressure change in the gas generation chamber results in a pressure change in the membrane actuation chamber; and
- limiting the passage of gas from the gas generation chamber to the membrane actuation chamber with a barrier shaped and configured to at least partially block gas from entering the membrane actuation chamber.

19. The method of claim 18, wherein limiting the passage of gas comprises at least partially blocking the gas with a barrier spanning the width of an opening to a passageway extending between the gas generation chamber and the membrane actuation chamber.

20. The method of claim 19, wherein the barrier is disposed within the gas generation chamber.

21. The method of claim 18, wherein the barrier directs gas bubbles away from the opening with obliquely-extending surfaces.

22. The method of claim 18, wherein the barrier is one of a piston and a wall structure.

* * * * *